United States Patent
Mullani

(10) Patent No.: US 8,177,808 B2
(45) Date of Patent: May 15, 2012

(54) VEIN HOLDER

(76) Inventor: Nizar A. Mullani, Sugar Land, TX (US)

( * ) Notice: Subject to any disclaimer, the term of this patent is extended or adjusted under 35 U.S.C. 154(b) by 453 days.

(21) Appl. No.: 11/705,530

(22) Filed: Feb. 13, 2007

(65) Prior Publication Data

US 2008/0195142 A1   Aug. 14, 2008

(51) Int. Cl.
*A61B 17/00* (2006.01)
(52) U.S. Cl. ...................................................... 606/201
(58) Field of Classification Search .......... 604/115–118, 604/174; 606/201, 213–217; 128/861, 888, 128/848, 859, 862; 433/6, 37; D24/181
See application file for complete search history.

(56) References Cited

U.S. PATENT DOCUMENTS

| | | | |
|---|---|---|---|
| 2,234,961 A | 3/1941 | Canada | |
| 3,324,854 A | 6/1967 | Weese | |
| 3,527,219 A * | 9/1970 | Greenberg | 433/25 |
| 4,314,568 A | 2/1982 | Loving | |
| 4,834,802 A | 5/1989 | Prier | |
| 5,165,424 A * | 11/1992 | Silverman | 128/861 |
| 5,415,647 A | 5/1995 | Pisarik | |
| 5,460,612 A | 10/1995 | Madore | |
| 5,601,596 A | 2/1997 | Lam | |
| 5,620,419 A | 4/1997 | Lui et al. | |
| 5,911,707 A | 6/1999 | Wolvek et al. | |
| 6,318,371 B1 * | 11/2001 | Tyszkiewicz | 128/859 |
| 6,652,487 B1 | 11/2003 | Cook | |
| 6,673,091 B1 | 1/2004 | Shaffer et al. | |
| 2004/0015130 A1 | 1/2004 | Neumann | |
| 2008/0138755 A1 * | 6/2008 | Jansheski et al. | 433/6 |
| 2008/0138766 A1 * | 6/2008 | Jansheski | 433/140 |

* cited by examiner

*Primary Examiner* — Ryan Severson
*Assistant Examiner* — Ashley Cronin
(74) *Attorney, Agent, or Firm* — Welsh Flaxman & Gitler LLC

(57) ABSTRACT

The vein holder has an upright wall forming a central opening. The central opening is large enough to allow easy access by a needle. A bottom flange extends outwardly from the wall and rests against the patient's skin. It is the bottom surface of the flange 14 which holds the skin tight to prevent movement of the vein relative to the skin. In addition, pressure applied by the vein holder closes the vein at an end away from the syringe opening.

3 Claims, 1 Drawing Sheet

VEIN HOLDER

BACKGROUND OF THE INVENTION

Medical procedures often require the use of a needle and syringe for the injection of medicine into a patient or the collection of a blood sample. Often these procedures require the needle to directly access a vein or artery. The ease in doing so depends on the skill and experience of the health provider, the accessability of the patient's veins and whether the patient is prone to move during the procedure.

Devices have been developed to help the health care provider in accurately placing a needle and syringe. One such device is disclosed in U.S. Pat. No. 5,911,707 (Wolvek et al.), disclosing a needle guide having a body with fingers extending therefrom to create openings at either end. Support members 30, 32 facilitate insertion of a needle. Also, U.S. Pat. No. 4,314,568 (Loving) discloses a vascular stabilizer having a flat body with a central slot 18.

In patients where access to veins is difficult, health providers sometimes resort to using a tourniquet in order to make the veins more pronounced and easier to access. In older patients this may cause veins to rupture due to high back pressure caused by the tourniquet. Another problem with older patients is a tendency of the veins to move, making the accurate placement of a needle more difficult.

It is an object of the invention to provide a vein holder allowing for the easy access of a vein by a needle.

It is another object of the invention to provide a vein holder stretching the skin to stabilize the position of the vein relative to the skin.

It is yet another object of the invention to provide a vein holder which does not utilize a tourniquet. It is still another object of the invention to provide a vein holder which may be held in place by one hand.

These an other objects of the invention will become apparent to one of ordinary skill in the art after reading the disclosure of the invention.

SUMMARY OF THE INVENTION

The vein holder has an upright wall forming a central opening. The central opening is large enough to allow easy access by a needle. A bottom flange extends outwardly from the wall and rests against the patient's skin. It is the bottom surface of the flange 14 which holds the skin tight to prevent movement of the vein relative to the skin. In addition, pressure applied by the vein holder closes the vein at an end away from the syringe opening.

DETAILED DESCRIPTION OF THE INVENTION

Figure 1:
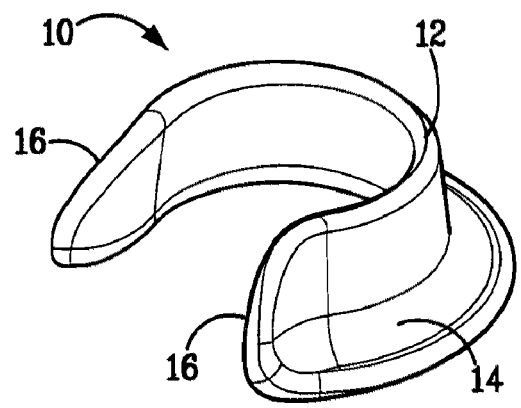
FIG. 1 is a perspective view of the vein holder.

FIG. 1 shows the vein holder 10 having the upstanding wall 12 forming a central opening. The upstanding wall may be any shape as long as a central opening is formed. In FIG. 1 the upstanding wall has an arcuate shape allowing for the more comfortable grip by a health provider with one hand.

A bottom flange 14 extends outwardly from the wall 12. The bottom flange will be discussed in further detail below. The end 16 of the upstanding wall have a gradually decreasing height so that the top edge of the wall 12 transitions into the side edge of the bottom flange 14.

Figure 2:
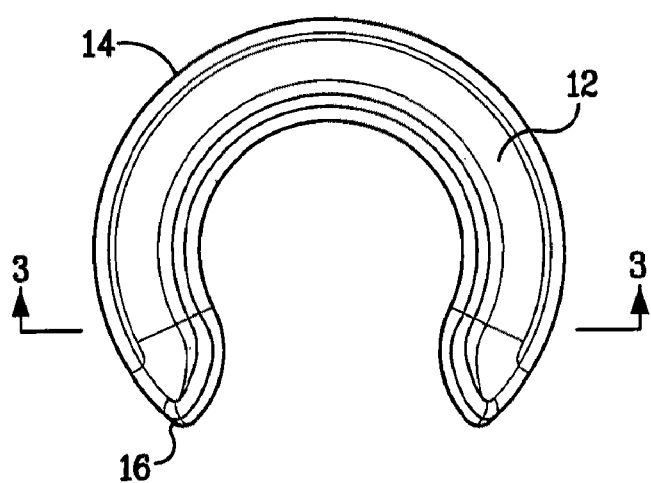
FIG. 2 is a top view of the vein holder.

FIG. 2 depicts a top view of the vein holder. In this view, the C-shape of the vein holder is clearly depicted. The central opening formed by the wall 12 and the space between the end 16 provides the health care provider ample room to both locate a vein and access the vein with a needle and syringe.

Figure 3:
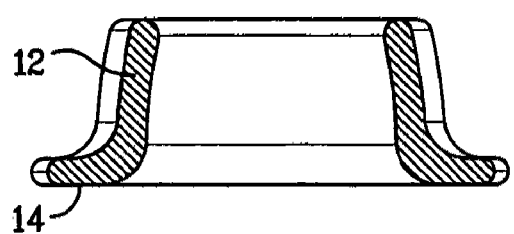
FIG. 3 is a cross-sectional view along 3-3 of FIG. 2.

FIG. 3 shows a cross-sectional view along line 3-3 of FIG. 2. In this view, the bottom surface of the flange 14 is seen. The bottom surface of the flange contacts the skin and serves to both hold the skin within the central opening tight and apply pressure to close the vein to the access. Ideally, the vein will be closed by a portion of the bottom flange which is opposite the space between the end 16 giving the health care provider the best possible view and room in order to access the vein.

The vein holder can be held by one hand, freeing the health care provider's other hand to manipulate the needle and syringe. The vein holder simultaneously the skin tight to prevent movement of the vein relative to the skin and applies pressure to close the vein to make the vein easier to access.

While the invention has been described with reference to preferred embodiment, a variation to modifications would be apparent to one of ordinary skill in the art. The invention encompasses such variations and modifications.

What is claimed is:

1. A vein holder consisting of:
a single upwardly extending wall having a top surface, a bottom surface, a first end, a second end and a bottom portion, said upwardly extending wall extending between said bottom surface and said top surface, wherein the ends of the upwardly extending wall have a gradually decreasing height,
a single flange provided around the outer periphery of said bottom portion, allowing a user's finger and thumb to rest upon said flange, wherein the upwardly extending wall extends substantially perpendicular to a bottom plane of the flange,
said upwardly extending wall forming a central opening, and
a space between the first end and the second end allowing access to the central opening, wherein when the user holds said flange, the user's finger and thumb would be protected from an accidental needle stick by said upwardly extending wall.

2. The vein holder in accordance with claim 1, wherein said upwardly extending wall is arcuate.

3. The vein holder in accordance with claim 1, wherein said upwardly extending wall is C-shaped.

* * * * *